(12) United States Patent
Obara et al.

(10) Patent No.: US 7,593,564 B2
(45) Date of Patent: Sep. 22, 2009

(54) METHOD AND APPARATUS FOR REVIEWING DEFECT OF SUBJECT TO BE INSPECTED

(75) Inventors: Kenji Obara, Kawasaki (JP); Kazuo Aoki, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 742 days.

(21) Appl. No.: 11/272,897

(22) Filed: Nov. 15, 2005

(65) Prior Publication Data

US 2006/0104500 A1 May 18, 2006

(30) Foreign Application Priority Data

Nov. 17, 2004 (JP) .............................. 2004-332811

(51) Int. Cl.
*G06K 9/00* (2006.01)
(52) U.S. Cl. .................................................... 382/141
(58) Field of Classification Search ........................ None
See application file for complete search history.

(56) References Cited

U.S. PATENT DOCUMENTS 4,589,140 A * 5/1986 Bishop et al. ............... 382/148

FOREIGN PATENT DOCUMENTS

| JP | 07-201946 | 8/1995 |
|---|---|---|
| JP | 08-220005 | 8/1996 |
| JP | 2000-030652 | 1/2000 |
| JP | 2000-215839 | 8/2000 |
| JP | 2000-222575 | 8/2000 |
| JP | 2001-338601 | 12/2001 |
| JP | 2004-163174 | 6/2004 |

* cited by examiner

*Primary Examiner*—Matthew C Bella
*Assistant Examiner*—Alex Liew
(74) *Attorney, Agent, or Firm*—McDermott Will & Emery LLP

(57) ABSTRACT

Absolute coordinates designate position coordinates of a defect of a calibrating substrate, and inspection coordinates designate position coordinates of the defect of the calibrating substrate detected by an inspection apparatus. A deviation of the inspection coordinates with respect to the absolute coordinates is an error included in the inspection coordinates. When "nonrandom errors" are removed from the inspection coordinates, a "random error" is left in the inspection coordinates. The view size for defect search in a defect reviewing apparatus is set based on the random error. Further, a defect for fine alignment is selected based on the tendency of a detected value of the defect size of the calibrating substrate detected by the inspection apparatus.

4 Claims, 8 Drawing Sheets

FIG.11

| REGISTERED INSPECTION APPARATUS LIST | | |
|---|---|---|
| INSPECTION APPARATUS NAME | REGISTRATION DATE | REMARKS |
| FOREIGN MATTER INSPECTION MACHINE NO. 1 | 01/04/2004 | FIRST FLOOR, REGISTRANT: SUZUKI |
| FOREIGN MATTER INSPECTION MACHINE NO. 2 | 05/06/2004 | SECOND FLOOR, REGISTRANT: SATO |
| FOREIGN MATTER INSPECTION MACHINE NO. 3 | 15/08/2004 | THIRD FLOOR, REGISTRANT: INOUE |
| PATTERN INSPECTION MACHINE NO. 1 | 25/05/2004 | FIRST FLOOR, REGISTRANT: SUZUKI |

HISTORY  DETAIL

FIG.12

| REGISTRATION DATE AND TIME | COMMENT |
|---|---|
| | REGISTRATION HISTORY |
| | INSPECTION APPARATUS NAME   FOREIGN MATTER INSPECTION MACHINE NO. 1 |
| 05/03/2003 10:15 | REGISTRANT: SUZUKI |
| 08/09/2003 09:05 | PERIODIC CALIBRATION |
| 25/11/2003 18:56 | RECALIBRATION DUE TO STAGE REPAIRING |
| 01/04/2004 13:20 | PERIODIC CALIBRATION |

RETURN   DETAIL

METHOD AND APPARATUS FOR REVIEWING DEFECT OF SUBJECT TO BE INSPECTED

BACKGROUND OF THE INVENTION

The present invention relates to a defect reviewing method and apparatus for zooming in on a defect of a thin-film device such as a semiconductor circuit substrate or a liquid crystal display substrate so as to review the defect.

A thin-film device such as a semiconductor circuit device, a liquid crystal display or a magnetic head is manufactured through a large number of processes. For example, the number of processes may reach several hundreds. Accordingly, these thin-film devices are completed by processing with a large number of processing machines. When there is an abnormality in a processing machine or something unsatisfactory in manufacturing conditions, the fraction defective of final products will be increased to drop the yield. Therefore, processed substrates are inspected by use of an inspection apparatus. Due to time and labor constraints, it is impossible to inspect all the processed substrates in each manufacturing process. Usually for each series of some processes, inspection is performed upon processed substrates sampled from each lot, each unit of processed substrates, or each combination of the lot and the unit. Here, the processed substrate means a minimum unit to be processed as a product. In the case of a semiconductor circuit device, the processed substrate designates one semiconductor wafer.

Inspection of processed substrates is categorized into foreign-matter inspection for inspecting the existence of foreign matters and visual inspection for inspecting the existence of pattern abnormality or the like. For example, in foreign-matter inspection of a semiconductor wafer, the surface of the semiconductor wafer is scanned with a laser so that the existence of scattering light is detected. Thus, information about the positions and number of foreign matters is obtained. In defect inspection for performing both the foreign-matter inspection and the visual inspection, for example, an image of a circuit pattern in one region of a semiconductor wafer is captured by an enlarging imaging optical system, and compared with an image of the same pattern in another region adjacent thereto, so as to detect abnormality of the pattern. Foreign matters and visual abnormality will be referred to as "defects" collectively. The visual abnormality includes adhesion of foreign matters, dirt, short-circuit and disconnection of wiring, etc.

Whether a processing machine is abnormal or not is often determined based on management parameters such as the number or density of defects detected by an inspection apparatus. When the number of defects exceeds a predetermined reference value, it is concluded that abnormality occurs in the processing machine. Each defect is magnified and picked up by a reviewing apparatus such as an optical microscope or a scanning electron microscope (hereinafter referred to as "SEM"). Thus, detailed information such as size, shape and texture is acquired, and inspection of details such as elementary analysis and sectional observation is performed. A processing machine contributing to the defect and the contents of failure thereof are specified based on the inspection of details. Then, based on the specified results, measures for the processing machine or processes are taken to prevent the yield from lowering.

In order to make such a reviewing work automatic and efficient, in recent years, there has been developed a reviewing apparatus having a function (automatic defect review, hereinafter referred to as "ADR") of automatically acquiring magnified images of foreign matters and defects based on inspection data from a foreign-matter inspection apparatus or a visual inspection apparatus.

JP-A-2000-30652 discloses an example of such a reviewing apparatus. JP-A-7-201946 discloses a method for performing automatic defect classification (hereinafter referred to as "ADC") on acquired images in conformity with specific rules.

When a defect of a semiconductor wafer is detected by an inspection apparatus and a magnified image of the defect is picked up by a reviewing apparatus, semiconductor wafer alignment is performed. The semiconductor wafer alignment means alignment between a stage coordinate system and a semiconductor wafer coordinate system in the inspection apparatus and the reviewing apparatus. The stage coordinate system depends on movable axes of a stage of each piece of apparatus. Therefore, the stage coordinate system is peculiar to each piece of apparatus. The semiconductor wafer coordinate system depends on each individual semiconductor wafer. In the case of a semiconductor wafer having a pattern formed therein, the semiconductor wafer coordinate system is generally defined along a die of the pattern. On the other hand, in the case of a semiconductor wafer having no pattern, the semiconductor wafer coordinate system is defined based on the positional relationship between the contour of the semiconductor wafer and a V notch or orientation flat thereof. When alignment between the stage coordinate system and the semiconductor wafer coordinate system is performed in the inspection apparatus and the reviewing apparatus respectively in their corresponding positions on the semiconductor wafer, the coordinate system in inspection with the inspection apparatus coincides with the coordinate system in review with the reviewing apparatus.

In fact, however, defect coordinate data output from the inspection apparatus include a semiconductor wafer alignment error or a defect detection position error at the time of inspection. Therefore, in spite of the semiconductor wafer alignment performed in the reviewing apparatus, a desired defect may not always come into view.

ADR is generally executed in consideration of such errors. That is, even when defect coordinate data output from the inspection apparatus include an error, the size of an observation view of a defect search image in the reviewing apparatus is selected so that the defect comes into the observation view. The position of the defect is searched in the defect search image, and a magnified image is picked up around the search position. Thus, a defect image is acquired.

However, when the defect coordinate data output from the inspection apparatus include a large error, the view size of the defect search image has to be set to be larger. Accordingly, the area ratio of the defect portion to the screen becomes smaller. Therefore, the probability of failure in recognizing the defect portion increases so that the reliability of the search is lowered. It is therefore desired that the view size of the search image in the reviewing apparatus is as small as possible. In the background art, the view size of the search image in the reviewing apparatus is determined by user's trial and error. Specifically, the view size is changed while observing the image in a plurality of defect coordinate positions. Thus, the view size is determined so that the defect is actually included in the screen.

There is another case where the defect coordinates output from the inspection apparatus are compared with the coordinates of a defect observed actually by the reviewing apparatus so as to perform fine adjustment on an error of the defect coordinates. This will be hereinafter referred to as "fine alignment". The fine alignment is specifically performed as follows. First, the center of the observation view in the reviewing apparatus is moved to the position of the defect coordinates output from the inspection apparatus, and a defect existing near the region of the observation view is searched. The position of the detected defect is specified. Such an operation is performed once or repeated a plurality of times. Coordinate transformation is performed to minimize an error between the specified coordinates of the actual defect position and the defect coordinates output from the inspection apparatus. A method for efficiently performing this fine alignment is disclosed in JP-A-2001-338601.

Further, JP-A-8-220005, JP-A-2000-215839 and JP-A-2000-222575 disclose methods for correcting an error of defect coordinates using a calibrating wafer.

SUMMARY OF THE INVENTION

When there is an error in the defect coordinates output from the inspection apparatus as described above, the view size for defect search in the defect reviewing apparatus cannot be selected efficiently. In addition, fine alignment cannot be carried out efficiently. Accordingly, a heavy load is imposed on the user. Further, since user's determination is involved, the reliability of correction differs from one worker to another.

An object of the present invention is to provide an apparatus and a method for reviewing a defect, in which the foregoing problems belonging to the background art are solved.

Another object of the present invention is to provide a method and an apparatus for reviewing a defect, in which an error of defect coordinates output from an inspection apparatus is corrected so that the view size for defect search and a defect for fine alignment can be selected easily in the defect reviewing apparatus.

According to the present invention, a calibrating substrate having a known defect is prepared, and the defect of the calibrating substrate is detected by the inspection apparatus. The position coordinates of the defect of the calibrating substrate will be referred to as "absolute coordinates", and the position coordinates of the defect of the calibrating substrate detected by the inspection apparatus will be referred to as "inspection coordinates". A deviation of the inspection coordinates with respect to the absolute coordinates is an error included in the inspection coordinates. When correctable errors, that is, "nonrandom errors" are removed from the inspection coordinates, an uncorrectable error, that is, a "random error" is left in the inspection coordinates. The view size for defect search in the defect reviewing apparatus is set based on the random error.

Further, according to the present invention, the correlation between the defect size of the calibrating substrate measured in advance and the detected value of the defect size of the calibrating substrate measured by the inspection apparatus is checked, and a defect having a high correlation is selected as a defect for fine alignment. Further, a defect in which the deviation of the inspection coordinates with respect to the absolute coordinates is constant regardless of the detected value of the defect size of the calibrating substrate is selected as a defect for fine alignment.

According to the present invention, the error of the defect coordinates output from the inspection apparatus can be corrected, and the view size for defect search and a defect for fine alignment can be selected easily in the defect reviewing apparatus.

Other objects, features and advantages of the invention will become apparent from the following description of the embodiments of the invention taken in conjunction with the accompanying drawings.

BRIEF DESCRIPTION OF THE DRAWINGS

FIG. 11 is a view showing a screen to call registered data according to the present invention by way of example; and FIG. 12 is a view showing a screen showing a history of the registered data according to the present invention by way of example.

DETAILED DESCRIPTION OF THE EMBODIMENT

Figure 1:
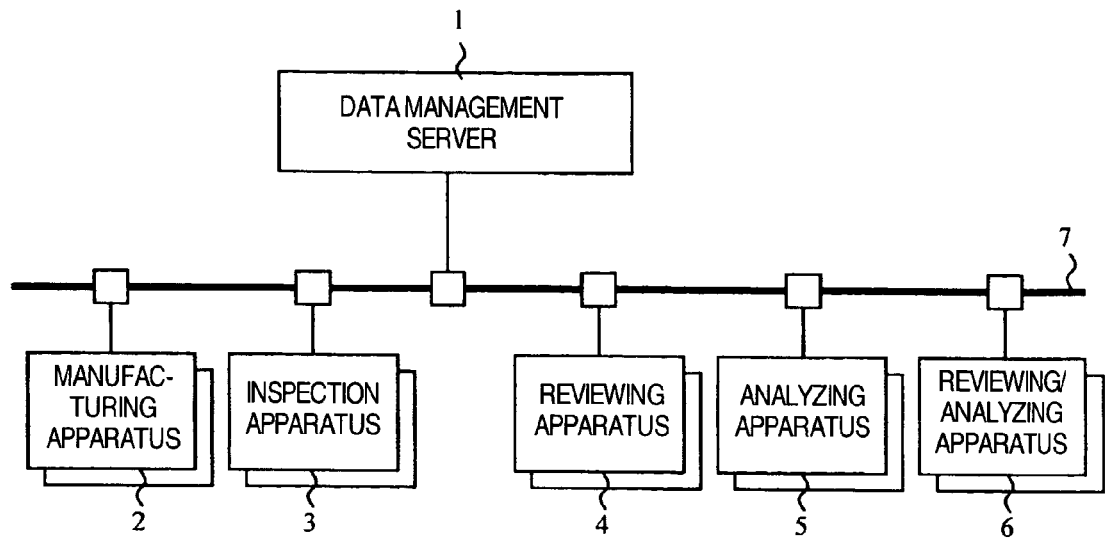
FIG. 1 is a diagram showing a semiconductor wafer manufacturing line including a reviewing apparatus according to the present invention by way of example.

An embodiment of the present invention will be described below with reference to the drawings. First, with reference to FIG. 1, description will be made on a specific example of a connection configuration of pieces of apparatus provided in a semiconductor wafer manufacturing line. The semiconductor wafer manufacturing line includes a data management server 1, semiconductor wafer manufacturing apparatus 2, inspection apparatus 3, reviewing apparatus 4, analyzing apparatus 5 and reviewing/analyzing apparatus 6. These pieces of apparatus are connected to one another through a network 7.

The data management server 1 manages data obtained by the inspection apparatus 3, the reviewing apparatus 4, the analyzing apparatus 5 and the reviewing/analyzing apparatus 6.

The manufacturing apparatus 2 includes various kinds of units to be used for manufacturing a semiconductor wafer, such as an exposure unit, an etching unit, etc. The inspection apparatus 3 inspects a semiconductor wafer and detects the position of a defect, the size of the defect, and so on. For example, the inspection apparatus 3 may specify or detect the position of a defect in either of the following two methods. In the first method, the inspection apparatus 3 scans the semiconductor wafer with a beam spot of light and specifies the position of a defect from the degree of diffused reflection of the light. In the second method, the inspection apparatus 3 compares an inspection image with a reference image. Of the inspection image, a portion different from the reference image is regarded as a defect, and the position of the defect is detected. Since the methods for detecting the defect have been known, details of the methods will not be described here. The inspection apparatus 3 sends coordinate data of the defect position to the reviewing apparatus 4, the analyzing apparatus 5 and the reviewing/analyzing apparatus 6 directly or through the data management server 1.

The reviewing apparatus 4 displays and observes the defect based on the defect position obtained by the inspection apparatus 3. For example, the reviewing apparatus 4 moves a stage mounted with the semiconductor wafer, positions a desired defect on the semiconductor wafer based on the coordinate data of the defect position, and then observes the defect.

The reviewing apparatus 4 may be a scanning electron microscope (SEM), an optical microscope using a visible light, a microscope using an ultraviolet light, or the like. Any apparatus may be used regardless of the kind of energy to be used, the intensity of the energy or the way to make the energy visible if the apparatus has a function capable of magnifying and picking up an image. The analyzing apparatus 5 performs elementary analysis, for example, using EDX or Auger electron spectroscopy, based on the coordinate data of the defect position. The Auger electron spectroscopy is a generally well known method for detecting and analyzing Auger electrons radiated from a target when the target is irradiated with an electron beam. The reviewing/analyzing apparatus 6 performs defect observation and elementary analysis based on the coordinate data of the defect position.

These pieces of apparatus for inspection, observation and analysis do not have to be separated from one another. A plurality of functions may be combined. For example, inspection and review (observation) may be made to be able to be carried out in one and the same piece of apparatus. Although description has been made on the configuration in which these pieces of apparatus are connected on the semiconductor wafer manufacturing line by way of example, any connection configuration may be used if data can be used among pieces of apparatus.

Figure 2:
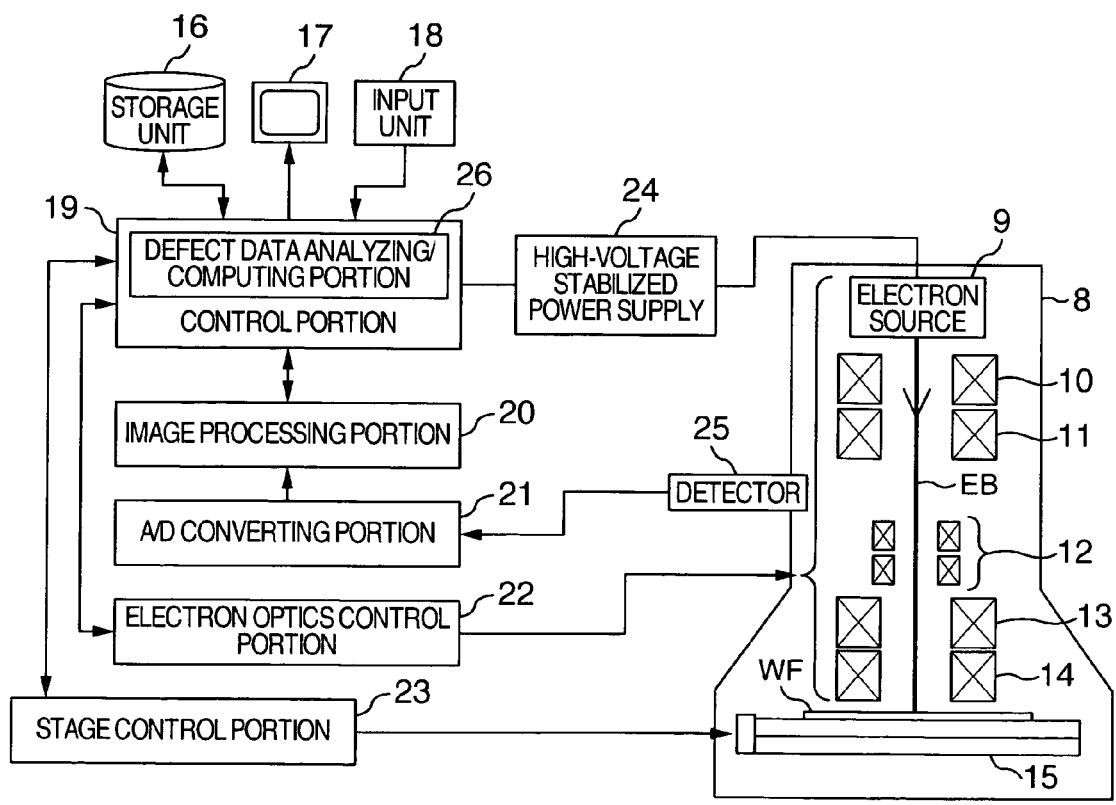
FIG. 2 is a diagram showing the configuration of the reviewing apparatus according to the present invention.

With reference to FIG. 2, the reviewing apparatus 4 using a scanning electron microscope (SEM) will be described by way of example. The reviewing apparatus 4 in this embodiment has an imaging unit 8. The imaging unit 8 includes an electron source 9, electron optics 10-14, an XY stage 15 and a detector 25. These parts constitute a scanning electron microscope (SEM). The optics 10-14 includes capacitor lenses 10 and 11, a deflection scanning coil 12, and objective lenses 13 and 14. The reviewing apparatus 4 further includes a storage unit 16, a monitor 17, an input unit 18, a control portion 19, an image processing portion 20, an A/D converting portion 21, an electron optics control portion 22, a stage control portion 23 and a high-voltage stabilized power supply 24. The control portion 19 includes a defect data analyzing/computing portion 26 for performing defect error analysis.

The defect error analysis performed by the defect data analyzing/computing portion 26 will be described later. In addition, the defect data analyzing/computing portion 26 may not be included in the reviewing apparatus 4. For example, the defect data analyzing/computing portion 26 may be provided as a function of the data management server 1 or may be included in each piece of the inspection apparatus 3.

An electron beam EB emitted from the electron source 9 is converged by the condenser lenses 10 and 11 and the objective lenses 13 and 14, and the electron beam EB is moved for a scan by the deflection scanning coil 12. A semiconductor wafer WF mounted on the XY stage 15 is irradiated with the electron beam EB moved for a scan. Due to this irradiation, secondary electrons or reflected electrons are released from the semiconductor wafer WF, and detected by the detector 25. An output from the detector 25 is processed by the A/D converting portion 21, and subjected to image processing by the image processing portion 20. An output from the image processing portion 20 is sent to the monitor 17 through the control portion 19, and a scanning electron microscope (SEM) image of the semiconductor wafer WF is displayed on the monitor 17.

The user inputs input items such as defect observation conditions etc. through the input unit 18. Input parameters are sent to the control portion 19. The control portion 19 sends control signals to the electron optics control portion 22 and the high-voltage stabilized power supply 24 so as to set photographing conditions of the scanning electron microscope (SEM). Defect coordinate data from the inspection apparatus 3 are sent to the control portion 19 through a not-shown network. The control portion 19 controls the stage control portion 23 based on the defect coordinate data from the inspection apparatus 3. The XY stage 15 is moved in the X and Y directions by the control of the stage control portion 23.

In the reviewing apparatus 4, based on the defect coordinate data from the inspection apparatus 3, the view size of the defect search image is set to locate the defect in a predetermined position within the observation view, for example, in a central position thereof. However, the defect coordinate data from the inspection apparatus 3 may include a detection error produced by the inspection apparatus 3 itself as described previously. When the defect coordinate data includes an error, the defect is displayed with a displacement from the central position of the observation view. Particularly if the error is large, the defect will be placed out of the observation view.

The view size for defect search in ADR is set to always put the defect in the view even when the defect coordinate data include an error as described above. For example, as the error of the defect coordinate data is larger, it is necessary to increase the size of the observation view for defect search so that the defect is put into the view. With increase of the view size, the size of the observed image of the defect in the search image becomes smaller relatively. Thus, the reliability in defect search is degraded. On the other hand, when the error of the defect coordinate data is small, the size of the observation view of the defect search image can be reduced. As a result, the size of the observed image of the defect becomes larger relatively. Thus, the reliability in defect search is improved. That is, it is more advantageous in defect search that the error of the defect coordinate data is smaller.

The size of the error produced by the inspection apparatus 3 depends on a defect detection system used by the inspection apparatus 3, and depends on individuality differing from one inspection apparatus to another. Errors that may be produced by the inspection apparatus 3 can be classified into "nonrandom errors" such as a rotational error and an offset error and a "random error" produced at random. The "nonrandom errors" can be corrected as will be described below in detail. However, the "random error" cannot be corrected. Thus, the "random error" is dealt with by adjusting the low-magnification view size for defect search so as to place the defect in the observation view. Description will be made below on the method for dealing with "nonrandom errors" produced by the inspection apparatus 3.

According to the present invention, a calibrating semiconductor wafer is used for analyzing an error produced by the inspection apparatus. In the calibrating semiconductor wafer, (1) the coordinates of a defect, (2) the size of the defect and (3) the kind of the defect have been known. The coordinates of the defect are detected by an inspection apparatus or a reviewing apparatus having high accuracy or a known error. The coordinates of the defect of the calibrating semiconductor wafer obtained thus in advance will be hereinafter referred to as "absolute coordinates". The size of the defect designates the projected area or the maximum diameter of the defect. When the defect has a convex shape, the height of the defect may be used together. When the defect has a concave shape, the depth of the defect may be used together.

Any method for producing the defect may be used. For example, a pattern may be built in by etching or the like, or standard particles or the like may be used. When the defect is built in by etching with a mask, the coordinates of the defect can be obtained by an input value to an exposure unit. In this case, the accuracy of the position of the defect depends on the accuracy of the exposure unit. The accuracy of the exposure unit is one or more digits higher than the positioning accuracy of the inspection apparatus or the reviewing apparatus. Accordingly, the coordinates of the defect obtained by the exposure unit are accurate enough to be used as reference coordinates. On the other hand, when the standard particles are used, the coordinates of the defect are measured in advance by an apparatus having a stage higher in accuracy than the inspection apparatus or the reviewing apparatus.

The procedure to analyze an error using the calibrating semiconductor wafer will be described with reference to FIG. 3. First, in STEP 100, the calibrating semiconductor wafer is inspected by an inspection apparatus to be analyzed. The coordinates of the defect obtained here will be hereinafter referred to as "inspection coordinates". Next, in STEP 101, the scanning electron microscope (SEM) serving as the reviewing apparatus (hereinafter referred to as "reviewing scanning electron microscope") reads inspection data including the "inspection coordinates" of the defect from the inspection apparatus. Next, in STEP 102, the XY stage 15 is moved to align the semiconductor wafer by the reviewing scanning electron microscope. Next, in STEP 103, the defect is searched near the "inspection coordinates" by the reviewing scanning electron microscope. This is attained by carrying out the aforementioned ADR.

Next, in STEP 104, it is determined whether the defect detected by the search is the defect built in in advance or not. This may be attained by using the aforementioned ADR technique or by comparing outline information of the detected defect with recorded outline information of the defect built in in advance. Any determination method may be used in STEP 104 if it can determine whether the detected defect is the built-in defect or not. By STEP 104, filtering can be performed to prevent analysis from being performed on foreign matter subsequently adhering to the calibrating semiconductor wafer, a defect produced subsequently, or a defect detected erroneously.

Here, when it is concluded that the detected defect is the built-in defect, the defect number of the defected defect and the defect coordinates calculated by the reviewing scanning electron microscope (SEM) are recorded in STEP 105. The defect coordinates obtained by the reviewing scanning electron microscope (SEM) will be hereinafter referred to as "SEM coordinates".

When it is concluded that the detected defect is not the built-in defect, or when no defect is detected, the routine of processing bypasses STEP 105 and moves to STEP 106.

In STEP 106, it is determined whether next data are present or not. That is, it is determined whether "inspection coordinates" of the next defect are present or not. When the next data are present, the next data are read in STEP 107, and the processing from STEP 103 to STEP 106 is repeated likewise. When the next data are absent, the routine of processing moves to STEP 108. In STEP 108, error analysis is performed on the defect recorded in STEP 105, and the result thereof is recorded. The error analysis includes estimation and correction of the error. The error analysis of the defect is executed by the defect data analyzing/computing portion 26.

Next, in STEP 109, analysis of conditions of a defect suitable for fine alignment is performed. The error analysis in STEP 108 and the analysis of conditions of a defect suitable for fine alignment in STEP 109 will be described in detail later.

The error analysis in STEP 108 will be described. Errors are classified into "nonrandom errors" and a "random error". First, "nonrandom errors" included in the inspection coordinates are estimated and removed. Thus, a "random error" is left in the inspection coordinates. The "random error" cannot be removed. Therefore, the view size of a defect search image is decided based on the "random error".

Examples of the "nonrandom errors" include a rotational error, a geometrical error, a dimensional error and an offset error. Description will be made below on the method for estimating the size of such a random error.

The rotational error, the geometrical error and the method for estimating those errors will be described with reference to FIG. 4. The rotational error designates an error in which the inspection coordinates displaced rotationally with respect to the absolute coordinates are output. Plots are drawn in a two-dimensional plane with the X-axis value designating the X-coordinate of the absolute coordinates of the defect and the Y-axis value designating the Y-direction displacement $\Delta y$ of the defect coordinates obtained by the relation $\Delta y$=[Y-coordinate of the inspection coordinates of the defect]−[Y-coordinate of the absolute coordinates of the defect]. When the inspection coordinates include no rotational error, these plots are distributed in parallel to the X axis. When the inspection coordinates include a rotational error, these plots are distributed with an inclination of an angle with the X axis, which angle is equal to the angle of the rotational error. Therefore, the distribution of the plots is approximated to a straight line, and the inclination of the straight line with respect to the X axis is regarded as a rotational error quantity. For example, least squares approximation can be used for approximation to the straight line. In order to correct the rotational error, rotational transform of the inspection coordinates may be performed to cancel the rotational error quantity.

The geometrical error designates a deviation between a rotational error with respect to the X axis and a rotational error with respect to the Y axis. In order to estimate the geometrical error, a rotational error quantity with respect to the Y axis is estimated likewise, and a difference between the rotational errors with respect to the two axes is obtained. In order to correct the geometrical error, it will go well if the rotational errors with respect to the X axis and the Y axis are corrected individually. Alternatively, it will go well if a mean of the rotational errors with respect to the X axis and the Y axis is regarded as a rotational error, and this rotational error is combined with the geometrical error and corrected. As for how to correct, it is preferable that a calculated value of a "random error" which will be described later is regarded as an evaluated value, and a method by which the evaluated value can be reduced is selected.

The dimensional error and the method for estimating the dimensional error will be described with reference to FIG. 5. The dimensional error designates misalignment of the scale of coordinates. The dimensional error is estimated and corrected after the correction of the rotational error described in FIG. 4. Therefore, the rotational error has been removed from the inspection coordinate data to be used here. In FIG. 5, the value of the X axis is set as the X component of the vector from the inspection apparatus origin to the point of the absolute coordinates of the defect. This vector will be hereinafter referred to as "defect vector". The inspection apparatus origin may differ from one kind of inspection apparatus to another. For example, the inspection apparatus origin may be the center of the semiconductor wafer or the left bottom of the chip matrix. Here, assume that the inspection apparatus origin depends on the kind of inspection apparatus.

On the other hand, plots are drawn in a two-dimensional plane with the value of the Y axis set as X-direction displacement $\Delta x$ of the defect coordinates obtained by the relation $\Delta x$=[X-coordinate of the inspection coordinates of the defect]−[X-coordinate of the absolute coordinates of the defect]. When no dimensional error is included, the plots are distributed in parallel to the X axis. When a dimensional error is included, the plots are not parallel to the X axis. Therefore, a straight line is applied to the plot group in the same manner as described in FIG. 4, so as to form a correction function of the X coordinate.

Further, as for the Y component, in the same manner, plots are drawn in a two-dimensional plane with the value of the X axis set as the Y component of the defect vector, and the value of the Y axis set as Y-direction displacement $\Delta y$ of the defect coordinates obtained by the relation $\Delta y$=[Y-coordinate of the inspection coordinates of the defect]−[Y-coordinate of the absolute coordinates of the defect]. The plots are approximated to a straight line in the same manner so as to calculate a correction function. Thus, the Y-coordinate value of the inspection coordinates is corrected likewise. In some characteristic of the inspection apparatus, the plots may be not arranged like a straight line. The plot group may be approximated to a function curve having a predetermined number of orders so as to form a correction function. The coordinate value of the inspection coordinates is corrected based on this correction function so as to cancel the dimensional error.

Next, the offset error, the "random error" and the method for estimating those errors will be described with reference to FIG. 6. The offset error designates an error in which the inspection coordinates are output to be displaced in the X- and Y-directions with respect to the absolute coordinates. The offset error is estimated and corrected after the correction of the rotational error in FIG. 4 and the dimensional error described in FIG. 5. Therefore, the rotational error and the dimensional error have been removed from the inspection coordinate data to be used here. In FIG. 6, plots are drawn in a two-dimensional plane with the value of the X axis set as X-direction displacement $\Delta x$ of the defect coordinates obtained by the relation $\Delta x$=[X-coordinate of the corrected inspection coordinates]−[X-coordinate of the absolute coordinates] and with the value of the Y axis set as Y-direction displacement of the defect coordinates obtained by the relation $\Delta y$=[Y-coordinate of the corrected inspection coordinates]−[Y-coordinate of the absolute coordinates].

Next, the density distributions of the plots projected on the X-axis and the Y-axis are calculated individually. Assume that the distribution of each displacement $\Delta x$, $\Delta y$ has random dispersion having no tendency, and conforms to a normal distribution. Assume that the distribution projected on each axis has a normal distribution curve. Then, the center of this normal distribution curve is defined as an offset error quantity. The X-coordinate value and the Y-coordinate value of the inspection coordinates are corrected to cancel the offset error. Thus, the rotational error, the dimensional error and the offset error which are "nonrandom errors" are removed, and only the "random error" is left. The distribution projected on each axis indicates the "random error".

Here, a value obtained by multiplying a standard deviation $\sigma$ of the normal distribution curve by a constant k is defined as the quantity of the "random error". For example, if the constant k is 3, 99.7% of the defect will be statistically included in the range of the quantity of the "random error".

A mean, a mode or the like may be used in place of the normal distribution. On the assumption that the mean of the distribution projected on each axis is an X- or Y-direction offset error, a value obtained by multiplying the standard deviation $\sigma$ calculated from the projected distribution by the constant k may be defined as the quantity of the "random error". Alternatively, on the assumption that the mode of the distribution projected on each axis is an X- or Y-direction offset error, a value obtained by multiplying the standard deviation $\sigma$ calculated from the projected distribution by the constant k may be defined as the quantity of the "random error".

Figure 4:
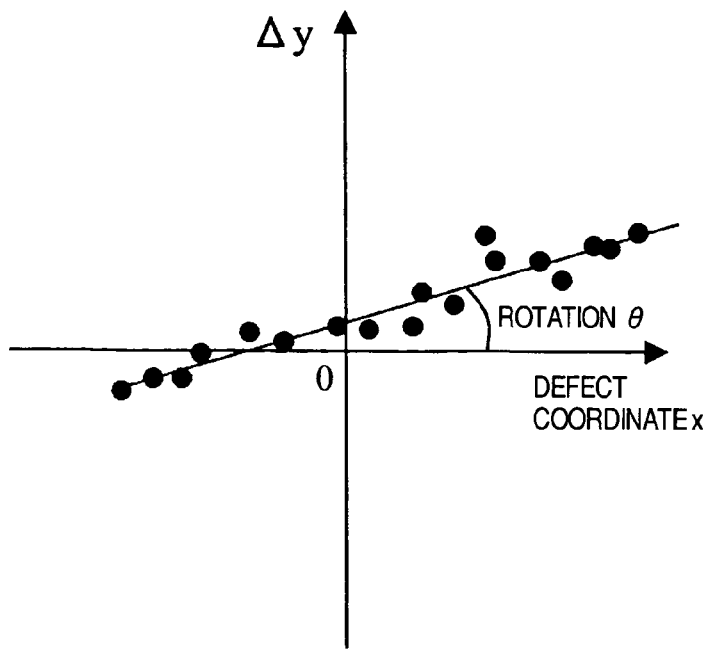
FIG. 4 is a graph for explaining a method for estimating a rotational error and a geometrical error in an error analysis technique according to the present invention.
Figure 5:
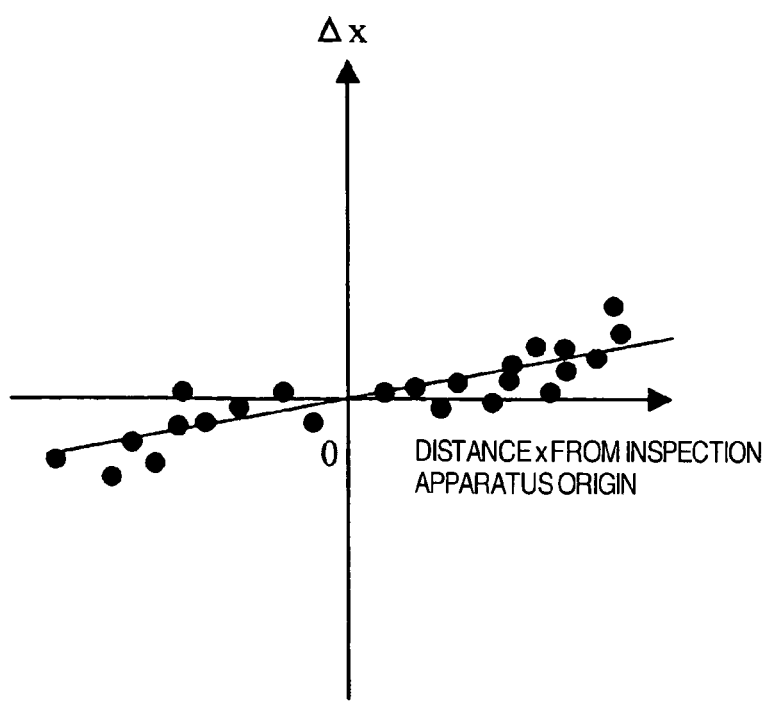
FIG. 5 is a graph for explaining a method for estimating a dimensional error in the error analysis technique according to the present invention.
Figure 6:
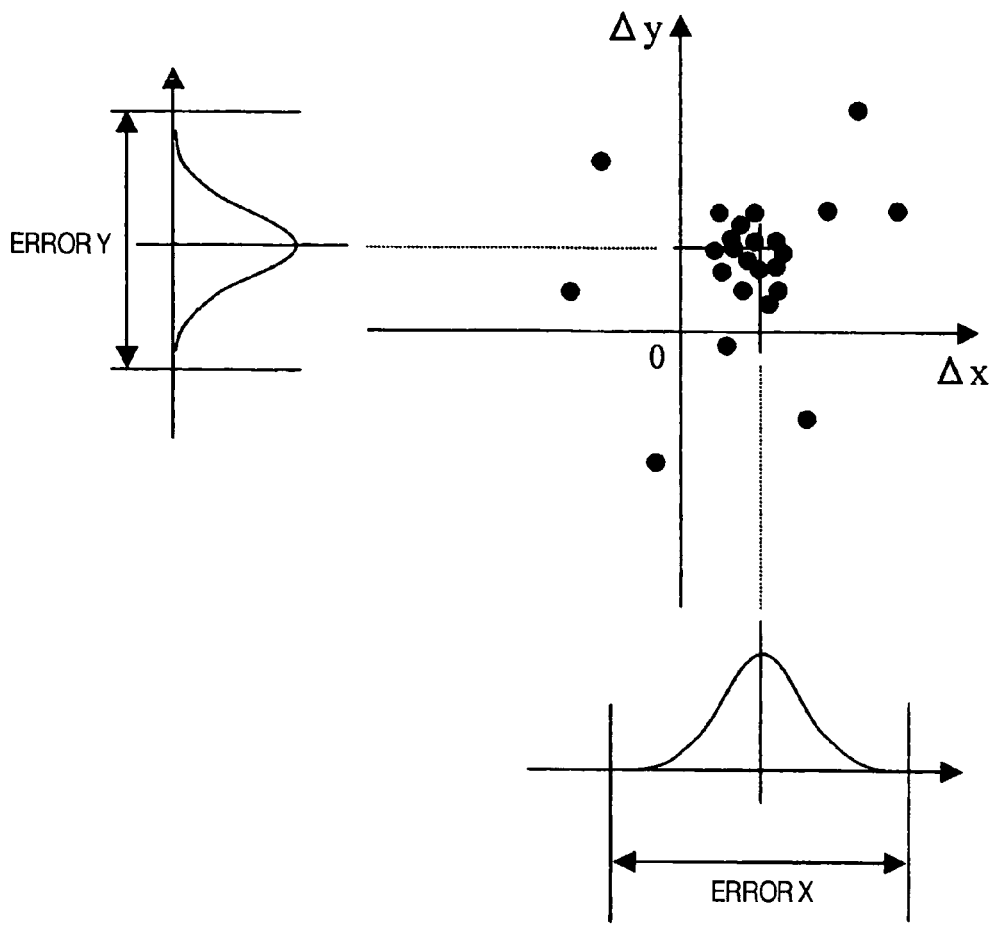
FIG. 6 is a graph for explaining a method for estimating an offset error and a "random error" in the error analysis technique according to the present invention.

When some "nonrandom error" is still included in the inspection coordinates obtained by the estimation and correction of the errors shown in FIGS. 4 to 6, another additional correction may be performed. Such a process may be repeated till the calculated corrected value converges. The "nonrandom errors" and the "random error" of the inspection coordinates calculated thus are stored as data proper to each inspection apparatus together with data such as the unique number of the inspection apparatus capable of uniquely identifying the inspection apparatus.

When the error analysis of the inspection coordinates is terminated, error analysis of the SEM coordinates is next executed in the same manner. Likewise, "nonrandom errors" and a "random error" of the SEM coordinates are stored as data proper to each scanning electron microscope (SEM) together with data such as the unique number of the scanning electron microscope (SEM) capable of uniquely identifying the scanning electron microscope (SEM). When the error analysis of the inspection coordinates and the error analysis of the SEM coordinates are terminated thus, the "random error" is calculated again by the method described in FIG. 6. The calculated "random error" is stored as a view size of a defect search image. That is, the view size of the defect search image to be finally stored in the scanning electron microscope (SEM) is calculated as an error in which the "random error" of the inspection apparatus and the "random error" of the reviewing scanning electron microscope (SEM) are combined.

In the method for determining the view size of the defect search image in the reviewing apparatus according to this embodiment, the view size is calculated by a convolutional operation using data of a "random error" of the inspection apparatus approximated to a normal distribution and data of a "random error" of the reviewing scanning electron microscope (SEM) apparatus approximated to a normal distribution. It is therefore possible to determine the optimum view size of the defect search image.

Next, description will be made on the method for analyzing the conditions of a defect suitable for fine alignment in STEP 109. In the reviewing apparatus 4, the defect search image is set based on the defect coordinate data from the inspection apparatus 3 so that the defect is placed in a predetermined position within the observation view, for example, in a central position thereof. However, when an error is included in the defect coordinate data, the defect is displayed to be displaced from the central position of the observation view. The fine alignment means a work for adjusting the position in the reviewing apparatus 4 so that the defect is placed in a predetermined position within the observation view, for example, in a central position thereof.

It is desired to use a small-error defect as a defect to be used for fine alignment. The conditions of a defect suitable for fine alignment designate conditions for selecting a defect suitable for use in fine alignment. The defect size may cause an error in the defect coordinates from the inspection apparatus 3. For example, an inspection apparatus of a dark field optical system detects diffusely-reflected light of oblique lighting. When the defect size is large, the diffusely-reflected light is so intensive that a detector may be saturated to produce an error in calculation of a detected position. Therefore, the method for limiting the conditions for selecting the defect will be described on the case of paying attention to the defect size by way of example.

In recent inspection apparatus, the defect size or the kind of defect is often output together with the coordinate data of the defect. However, for example, in an inspection apparatus of a dark field optical system, such defect size information is information about the intensity of a diffusely-reflected component converted into a defect size. Therefore, the output defect size may not always coincide with the real defect size. It can be considered that the reliability of the defect size differs from one kind of defect to another. Accordingly, the reliability of the defect size is evaluated for each kind of defect output by the inspection apparatus. For example, the evaluation is performed as follow.

Figure 7:
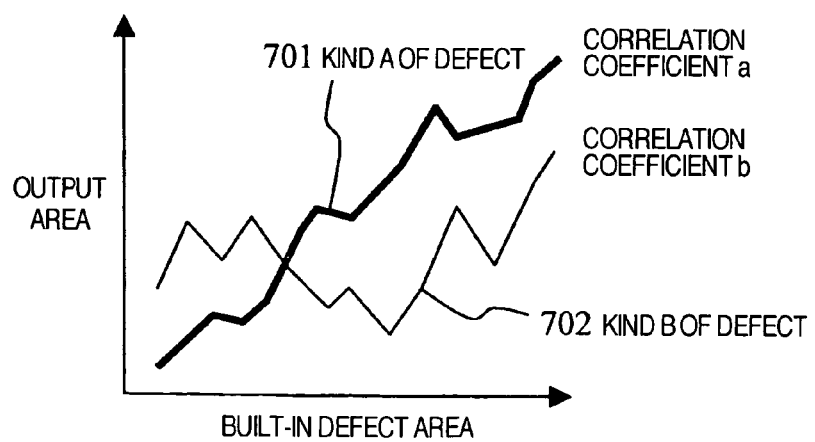
FIG. 7 is a graph for explaining the relationship between a defect size of a calibrating semiconductor wafer and an area value of a defect measured by an inspection apparatus.

First, as shown in FIG. 7, a graph whose ordinate designates the size of a defect built in a calibrating semiconductor wafer and whose abscissa designates the area value of the defect measured by an inspection apparatus is created in a two-dimensional plane for each kind of defect classified in accordance with the inspection apparatus. A correlation coefficient between the built-in defect size in the ordinate and the measured value of the area of the defect in the abscissa is calculated for each kind of defect. In the illustrated example, a curve 701 is a graph of a kind A of defect, and the correlation coefficient of the kind A of defect is a. A curve 702 is a graph of a kind B of defect, and the correlation coefficient of the kind B of defect is b. Assume that the correlation coefficient a of the kind A of defect is larger than the correlation coefficient b of the kind B of defect. That is, assume that a>b. In the case of the kind A of defect having a larger correlation coefficient, the measured value of the defect size can be regarded as higher in reliability. In the case of the kind B of defect having a smaller correlation coefficient, the measured value of the defect size can be regarded as lower in reliability.

Figure 8:
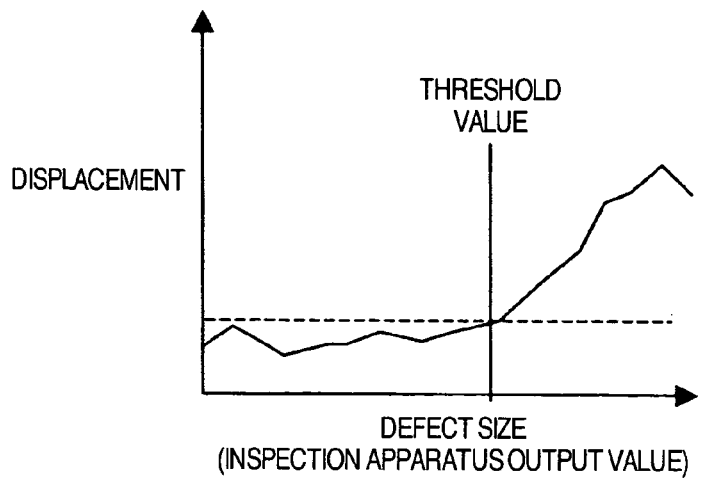
FIG. 8 is a graph for explaining the relationship between a measured value of a defect area obtained by the inspection apparatus and a displacement from absolute coordinates.

FIG. 8 is a graph created in a two-dimensional plane, in which only the kinds of defects whose correlation coefficients are larger than a predetermined threshold value are selected, and the abscissa designates a measured value of the defect area obtained by the inspection apparatus while the ordinate designates a displacement from the absolute coordinates. Here, for example, the displacement from the absolute coordinates is defined as a distance between the inspection coordinates and the absolute coordinates of a defect. As illustrated, there may be a tendency that the displacement is fixed in a range where the measured value of the defect size is smaller than a predetermined value, while the displacement increases with increase of the measured value of the defect size in a range where the measured value of the defect size is larger than the predetermined value. In such a case, the predetermined value is set as a threshold value. A defect whose defect size is smaller than the threshold value is selected as a defect for use in fine alignment. In such a manner, according to this embodiment, a defect small in error of a detected position and suitable for fine alignment can be selected based on the kind of defect and the measured value of the defect size output form the inspection apparatus.

When there is no change in the measured value of the defect size in spite of increase in displacement, a defect for fine alignment may be selected regardless of the measured value of the defect size. When the order of the displacement to be corrected is close to the order of the measured value of the defect size, it is difficult to specify which portion of a defect region was output as a defect position by the inspection apparatus. Thus, the position of the defect for fine alignment cannot be specified correctly. Therefore, a defect in which the order of the measured value of the defect size is equal to the order of the displacement to be corrected had better not be selected for fine alignment.

Here, as for the number of points where fine alignment should be performed, a required number of points may be statistically calculated in accordance with the magnitude of the "random error" after a threshold value is set for a reliable section in advance.

In the example of the error analysis of the defect coordinates of the inspection apparatus described with reference to FIG. 3, defect search is performed near the "inspection coordinates" obtained by the inspection apparatus, by the reviewing scanning electron microscope in STEP 103. As the method for performing the error analysis of the defect coordinates of the inspection apparatus simply and easily, such defect search by the reviewing scanning electron microscope (SEM) may be omitted only the coordinate analysis in which the "inspection coordinates" obtained by the inspection apparatus are compared with the "absolute coordinates" may be performed in place of the defect search. Thus, the procedure can be simplified. In this case, if the calibrating semiconductor wafer includes foreign matter adhering thereto subsequently, a defect produced subsequently, or a defect detected erroneously, error estimation will be made uncertain. Therefore, in the analysis described in FIGS. 4 to 6, any point deviant from the distribution of the plots is regarded as an abnormal point and precluded from the calculation. Thus, the influence of such a factor can be reduced.

Figure 3:
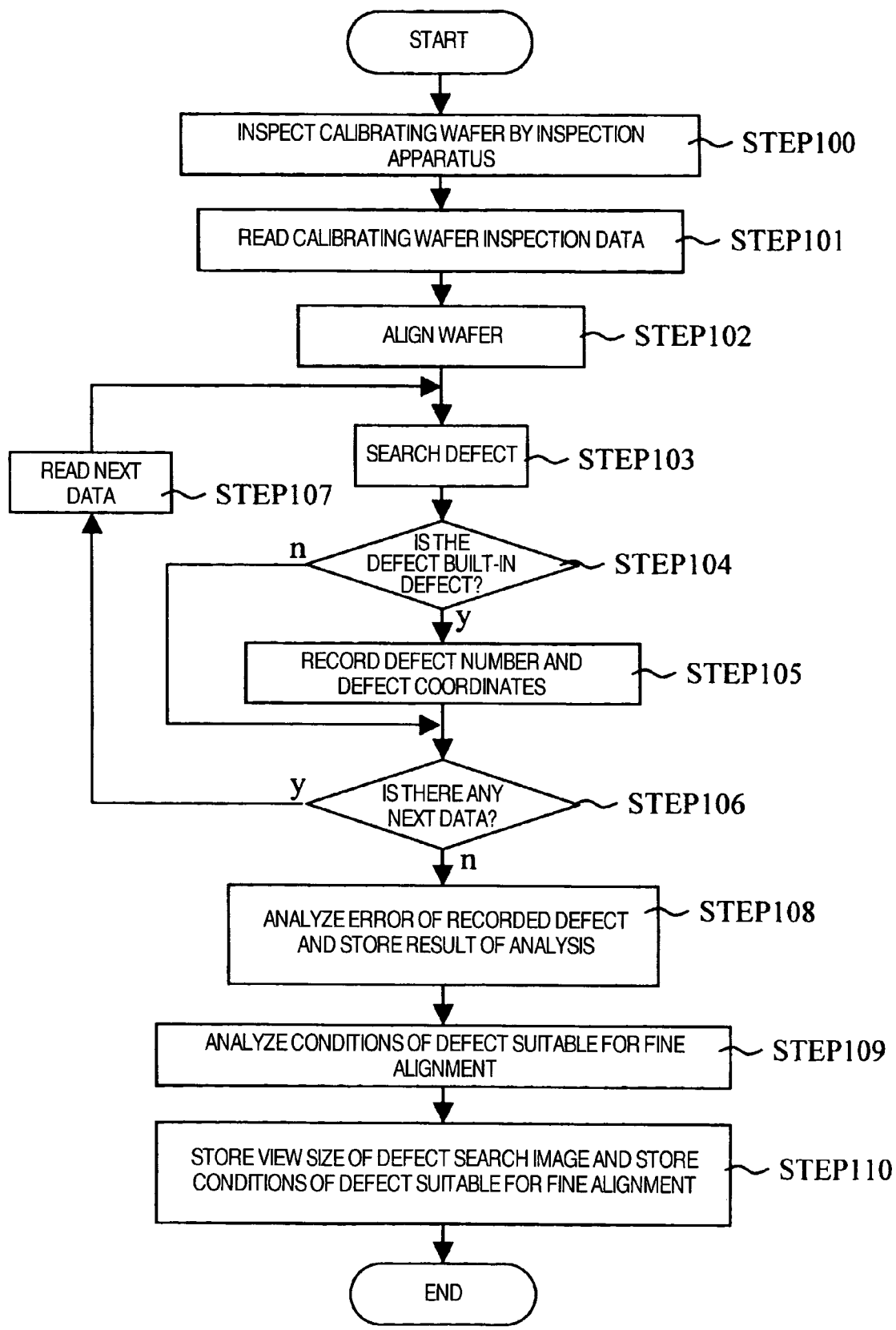
FIG. 3 is a flow chart for explaining the flow of processing for error analysis according to the present invention.

The error analysis of the defect described in FIG. 3 may be performed a plurality of times by one and the same inspection apparatus so as to evaluate the repeatability thereof. In this case, the coordinate position of the defect for fine alignment may be automatically calculated and represented to the user so that the user can properly correct error items low in repeatability. For example, when any error other than the offset error is high in repeatability, fine alignment may be performed at any position on the semiconductor wafer. When the rotational error is lower in repeatability, it is desired to perform fine alignment not only near the center but also in at least two points in the periphery of the semiconductor wafer. When the dimensional error is low in repeatability, it is desired to perform fine alignment in at least two concentric points around the inspection apparatus origin. In such a manner, the semiconductor wafer alignment position may be changed automatically in accordance with the result of evaluation of repeatability.

When the estimated error quantity of the "nonrandom errors" or the error estimated quantity of the "random error" is high in repeatability, it is not necessary to perform fine alignment whenever the semiconductor wafer is replaced. In such a manner, whether fine alignment is required or not may be determined in accordance with the result of evaluation of repeatability so as to automatically change over the sequence as to whether to perform fine alignment or not.

Figure 9:
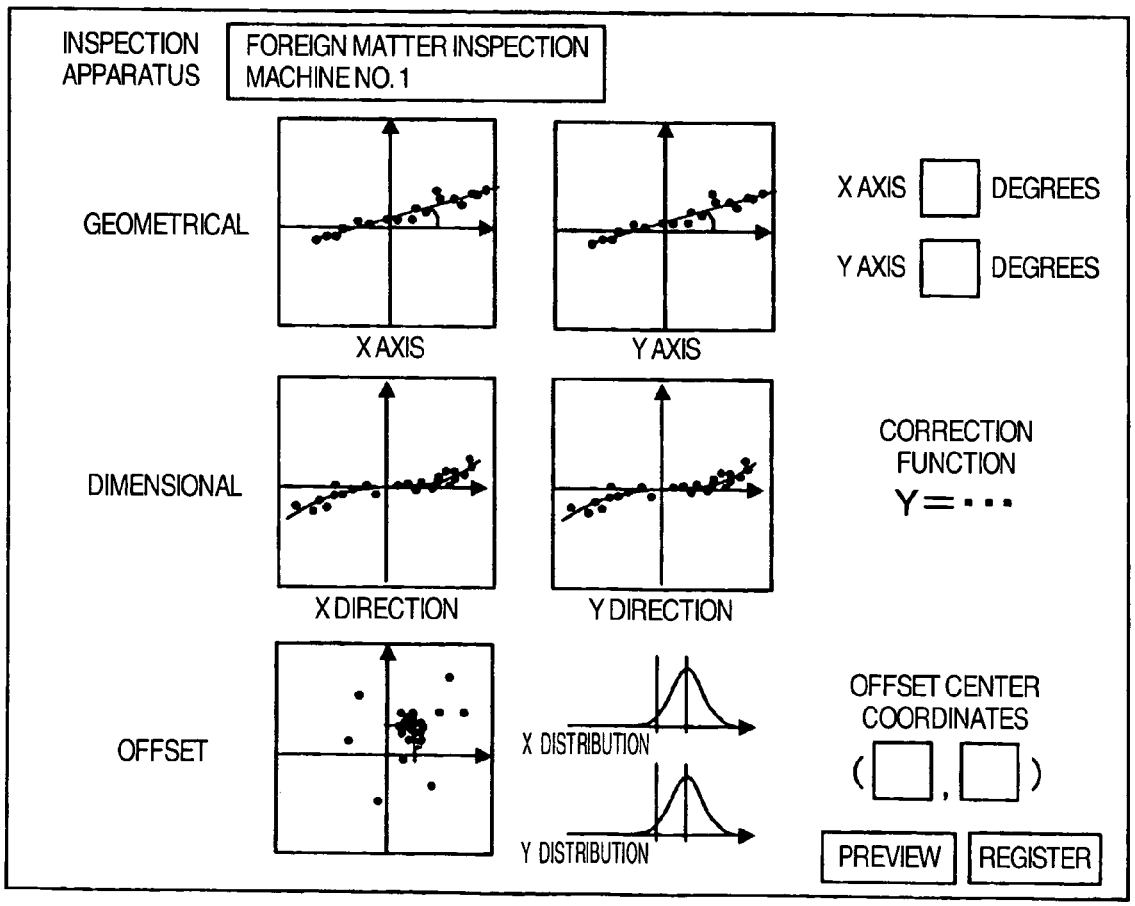
FIG. 9 is a view showing a screen showing estimated results of errors in defect coordinate data of the inspection apparatus according to the present invention by way of example.

Examples of screens displaying results of error analysis will be described with reference to FIGS. 9 to 12. FIG. 9 shows an example of a screen displaying estimated results of errors in defect coordinate data of an inspection apparatus. At least one of the aforementioned geometrical, dimensional and offset errors is displayed by a two-dimensional graph to be intelligible visually, together with the name or ID number of the inspection apparatus to be analyzed. In addition, calculated correction parameters may be displayed together. Correction results using the parameters may be displayed intelligibly. When a "register" button is pushed, the error data are registered in a database.

Figure 10:
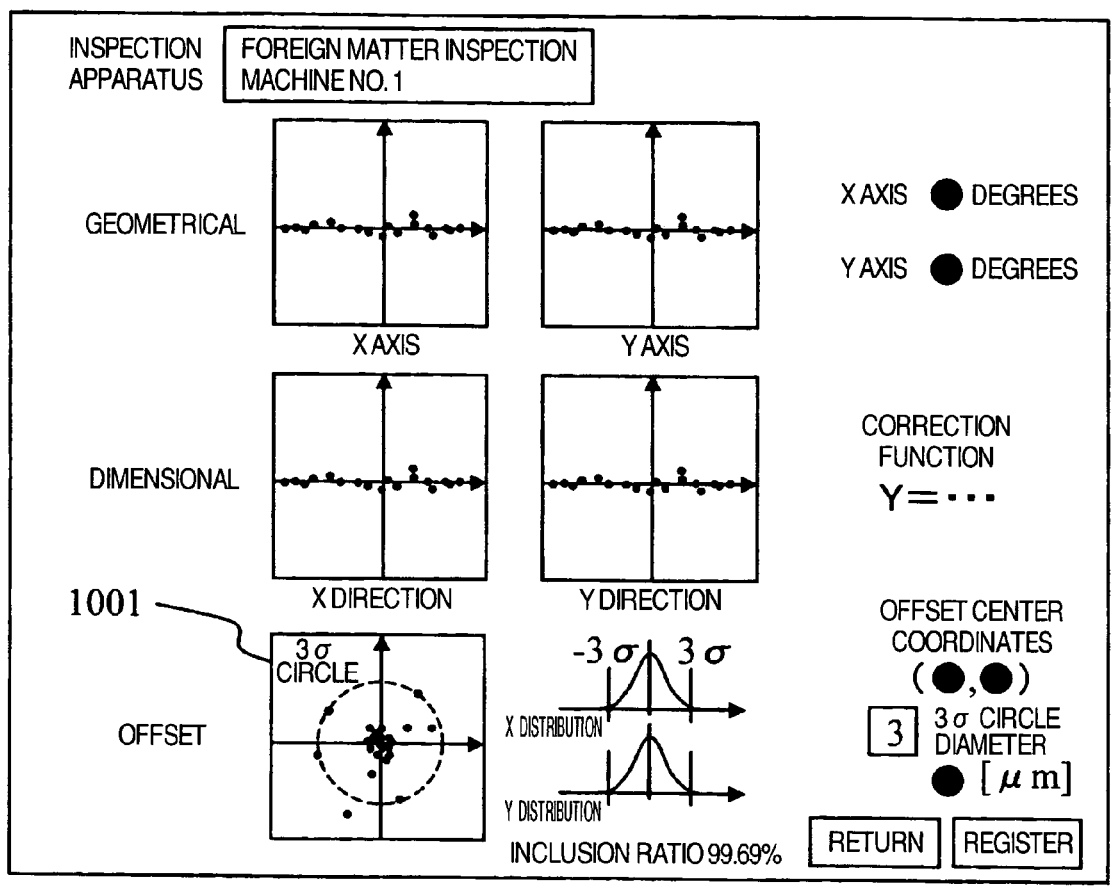
FIG. 10 is a view showing a screen showing corrected results of the errors in the defect coordinate data of the inspection apparatus according to the present invention by way of example.

FIG. 10 shows an example of a screen showing corrected results of errors in defect coordinate data of the inspection apparatus in FIG. 9. When a preview button is pushed on the screen in FIG. 9, the screen changes over to the screen in FIG. 10. In FIG. 10, the correction results of the aforementioned errors are shown in two-dimensional graphs respectively. Plots 1001 in a graph labeled "offset" show inspection coordinate data from which all the "nonrandom errors" have been removed. The dispersion of the plots 1001 expresses a "random error", which cannot be removed. Therefore, the view size for defect search in the reviewing scanning electron microscope (SEM) is determined based on the dispersion of the plots. On this screen, the user can input the view size in the form of a scale of a standard deviation $\sigma$ of the estimated dispersion. When the input value is k, a circle having a radius k$\sigma$ and showing a dispersion range is drawn in the graph in accordance with the value k, and the ratio of the number of defects included in this circle is displayed. The user adjusts the input constant k in accordance with the displayed ratio. The diameter of the circle corresponds to the view size of the defect search image. When the "register" button is pushed, the correction data are registered in the database.

FIG. 11 shows an example of a screen for calling registered data. This screen includes at least inspection apparatus names or inspection apparatus ID numbers, and registration dates. Those items of information may be displayed to be linked with desired information as shown in the remarks column of FIG. 11. It is also preferable that information as shown in FIGS. 9 and 10 can be called when a "detail" button is pushed on this screen. It is also preferable that corresponding inspection apparatus names, dates when correction data were registered, and desired comments linked with those items of information are displayed as shown in FIG. 12 when a "history" button is pushed. The screen of FIG. 12 may return to the screen of FIG. 11 when a "return" button is pushed. It is also preferable that information shown in FIGS. 9 and 10 at the time when a piece of information is selected on the list of FIG. 12 can be called when a "detail" button is pushed on the screen of FIG. 12 after the piece of information is selected.

Although the examples of screens to be displayed have been described for the inspection apparatus, correction information of the reviewing apparatus itself may be displayed.

Here, as a result of analysis in the method used for checking the conditions of a defect suitable for fine alignment, there may be a tendency that the displacement of coordinates increases in accordance with the defect size. In such a case, the view size of the defect search image may be made variable in accordance with the displacement. That is, when a defect satisfying the conditions with which the displacement is increased is included in data output from the inspection apparatus, the view size of the defect search image may be increased in accordance with the result of analysis so that the defect can be put in the image surely.

In addition, in the reviewing scanning electron microscope (SEM), the calibrating semiconductor wafer may be subjected to ADR periodically so as to update the correction quantity of each kind of error. Further, transition of each error with age may be monitored so that a warning can be given to ask for maintenance when the error is beyond a specification limit on design.

In addition, the size of an image to be used for defect search, that is, the number of pixels (picture elements) forming the image may be changed in accordance with the size of a smallest detectable defect registered in advance and the magnitude of the "random error" calculated in this inventive technique. From the point of view of image processing, the detectable defect size is expressed by pixels which are the smallest units forming an image. On the other hand, the view range of the image to be used for defect search is defined in accordance with the magnitude of the "random error". The detectable defect size depends on the image size with which the image is acquired in the view range. For example, assume that the number of pixels of the smallest detectable defect is 10 pixels from the point of view of image processing. When the image size is small and the size of the registered smallest detectable defect corresponds to 5 pixels, the registered defect cannot be detected. Therefore, when the image size is increased and set so that the size of the registered smallest detectable defect exceeds 10 pixels, the registered smallest defect to be detected can be detected.

Although the embodiment of the present invention has been described above, the present invention is not limited to the aforementioned embodiment. It will be understood for those skilled in the art that various changes can be made on the invention without departing the scope of the invention stated in the claims.

The invention claimed is:

1. A defect reviewing apparatus comprising:
   an input unit for inputting inspection information of a defect to be inspected, said inspection information being obtained by an inspection apparatus;
   a display unit for displaying a magnified image of said defect to be inspected, based on position coordinates of said defect, said position coordinates being input through said input unit; and
   a defect data analyzing/computing portion for analyzing errors included in said position coordinates of said defect, wherein:
   said defect data analyzing/computing portion determines a deviation of inspection coordinates with respect to absolute coordinates as an error caused by said inspection apparatus, estimates a random error based on said error, and sets a view size for defect search in said display unit based on said random error, when said absolute coordinates designate position coordinates of a defect in a known calibrating substrate, and said inspection coordinates designate position coordinates of said defect of said calibrating substrate detected by said inspection apparatus,
   said input unit inputs a detected value of a defect size of said calibrating substrate detected by said inspection apparatus, and
   said defect data analyzing/computing portion determines a correlation between said detected value of said defect size and a real value of said defect size measured in advance, and selects a defect in which said correlation is higher than a predetermined threshold value, as a defect suitable for fine alignment.

2. A defect reviewing apparatus comprising:
an input unit for inputting inspection information of a defect to be inspected, said inspection information being obtained by an inspection apparatus;
a display unit for displaying a magnified image of said defect to be inspected, based on position coordinates of said defect, said position coordinates being input through said input unit; and
a defect data analyzing/computing portion for analyzing errors included in said position coordinates of said defect, wherein:
said defect data analyzing/computing portion determines a deviation of inspection coordinates with respect to absolute coordinates as an error caused by said inspection apparatus, estimates a random error based on said error, and sets a view size for defect search in said display unit based on said random error, when said absolute coordinates designate position coordinates of a defect in a known calibrating substrate, and said inspection coordinates designate position coordinates of said defect of said calibrating substrate detected by said inspection apparatus,
said input unit inputs a detected value of a defect size of said calibrating substrate detected by said inspection apparatus, and
said defect data analyzing/computing portion selects a defect in which said deviation of said inspection coordinates with respect to said absolute coordinates is fixed regardless of said detected value of said defect size, as a defect suitable for fine alignment.

3. A defect reviewing method for inputting position coordinates of a defect obtained by an inspection apparatus and displaying a magnified image of said defect by means of a defect reviewing apparatus, the method comprising steps of:
preparing a calibrating substrate having a defect whose position has been known and whose coordinates are called absolute coordinates; and
detecting a position of said defect of said calibrating substrate by means of said inspection apparatus, and outputting said detected position as inspection coordinates,
wherein the method further comprises steps executed by a processor included in a defect data analyzing/computing portion disposed in said defect reviewing apparatus, the steps executed by the computer comprising:
comparing said inspection coordinates with said absolute coordinates, and determining a deviation between said inspection coordinates and said absolute coordinates as an error due to said inspection apparatus;
extracting nonrandom errors from said error, and removing said nonrandom errors from said inspection coordinates;
determining an error included in said inspection coordinates from which said nonrandom errors have been removed, as a random error;
setting a view size for defect search in said defect reviewing apparatus based on said random error included in said inspection coordinates;
determining a correlation between a detected value of a defect size of said calibrating substrate detected by means of said inspection apparatus and a real value of said defect size measured in advance; and
selecting a defect in which said correlation is higher than a predetermined threshold value, as a defect suitable for fine alignment.

4. A defect reviewing method for inputting position coordinates of a defect obtained by an inspection apparatus and displaying a magnified image of said defect by means of a defect reviewing apparatus, the method comprising steps of:
preparing a calibrating substrate having a defect whose position has been known and whose coordinates are called absolute coordinates; and
detecting a position of said defect of said calibrating substrate by means of said inspection apparatus, and outputting said detected position as inspection coordinates,
wherein the method further comprises steps executed by a processor included in a defect data analyzing/computing portion disposed in said defect reviewing apparatus, the steps executed by the processor comprising:
comparing said inspection coordinates with said absolute coordinates, and determining a deviation between said inspection coordinates and said absolute coordinates as an error due to said inspection apparatus;
extracting nonrandom errors from said error, and removing said nonrandom errors from said inspection coordinates;
determining an error included in said inspection coordinates from which said nonrandom errors have been removed, as a random error;
setting a view size for defect search in said defect reviewing apparatus based on said random error included in said inspection coordinates;
obtaining a deviation of said inspection coordinates with respect to said absolute coordinates; and
selecting a defect in which said deviation is fixed regardless of a detected value of a defect size of said calibrating substrate detected by means of said inspection apparatus, as a defect suitable for fine alignment.

* * * * *